United States Patent [19]

Fetzer et al.

[11] Patent Number: 5,587,135
[45] Date of Patent: Dec. 24, 1996

[54] PROCESS FOR THE CATALYTIC DECOMPOSITION OF DINITROGEN MONOXIDE IN A GAS STREAM

[75] Inventors: Thomas Fetzer, Speyer; Wolfgang Buechele, Ludwigshafen; Hermann Wistuba, Mannheim; Bernhard Otto, Limburgerhof; Gert Buerger, Mannheim; Paul Pijl, Frankenthal, all of Germany

[73] Assignee: BASF Aktiengesellschaft, Ludwigshafen, Germany

[21] Appl. No.: 403,835

[22] PCT Filed: Jan. 13, 1994

[86] PCT No.: PCT/EP94/00081

§ 371 Date: Mar. 24, 1995

§ 102(e) Date: Mar. 24, 1995

[87] PCT Pub. No.: WO94/16798

PCT Pub. Date: Aug. 4, 1994

[30] Foreign Application Priority Data

Jan. 21, 1993 [DE] Germany .................. 43 01 470.4

[51] Int. Cl.$^6$ .................................................. B01J 8/00

[52] U.S. Cl. ............................................... 423/239.1

[58] Field of Search .................. 423/239.1, 235

[56] References Cited

PUBLICATIONS

Angeletti et al. "Structure and Catalytic Activity of Co1–xAl$_2$O$_4$ Spinal Solid Solutions", 1977 (no month) pp. 1595–1603.

*Primary Examiner*—Steven Bos
*Assistant Examiner*—Thomas G. Dunn, Jr.
*Attorney, Agent, or Firm*—John H. Shurtleff

[57] ABSTRACT

A process for the catalytic decomposition of dinitrogen monoxide in a gas stream by contacting the gas stream at temperatures of 200°–900° C. and pressures of 0.1 to 20 bar with a catalyst free of noble metals, the catalyst being prepared by combining a spinel CuAl$_2$O$_3$ with another spinel-forming metal component selected from the group consisting of tin, lead, zinc, magnesium, calcium, strontium and barium or mixtures thereof in elemental form or as an oxide or salt, and calcining at temperatures of 300°–1300° C. and under pressures of 0.1–200 bar in order to at least partially liberate the copper from the spinel by replacement with the other metal component.

12 Claims, No Drawings

PROCESS FOR THE CATALYTIC DECOMPOSITION OF DINITROGEN MONOXIDE IN A GAS STREAM

The present invention relates to a process for the catalytic decomposition of dinitrogen monoxide which is pure or present in gas mixtures using a catalyst prepared by combining R-Al$_2$O$_4$ where R is an element of group Ib, VIIb or VIII of the Periodic Table of the Elements, with tin, lead, an element of group IIa or IIb of the Periodic Table of the Elements as an oxide or salt or in elemental form, and calcining at 300°–1300° C. under 0.1–200 bar.

A review of the energies of activation for the catalytic decomposition of dinitrogen monoxide (laughing gas) on oxide catalysts, especially on mixed oxides, is given in Catalysis Today 4 (1989) 235–251.

The catalysts described therein are unsatisfactory in terms of activity, or useful life, contain costly elements such as noble metals.

It is an object of the present invention to remedy the abovementioned disadvantages.

We have found that this object is achieved by a novel and improved process for the catalytic decomposition of dinitrogen monoxide which is pure or present in gas mixtures at 200°–900° C., which comprises employing a catalyst prepared by combining CuAl$_2$O$_4$ with tin, lead, an element of group IIa or IIb of the Periodic Table of the Elements as an oxide or salt or in elemental form, and calcining at 300°–1300° C. under 0.1–200 bar.

The process according to the invention can be carried out by preheating pure dinitrogen monoxide or gas mixtures containing it or off-gas containing it in a furnace or heat exchanger to the required reactor temperature of, as a rule, 200°–900° C., preferably 250°–800° C., particularly preferably 350°–700° C., and then passing it through a reaction tube packed with the catalyst described. The preheating of the reaction gas can also take place directly in the reaction tube in a preceding layer of inert material which is at the reaction temperature. The catalyst and/or inert material can be heated by using an external source of heat and/or the heat liberated in the decomposition of the dinitrogen monoxide.

It is possible to employ dinitrogen monoxide in extra pure form, or mixed with oxygen or air, or mixed with air containing large amounts of water and/or large amounts of other nitrogen oxides such as nitrogen monoxide and nitrogen dioxide or high concentrations of nitrogen oxides and other gases such as NO$_x$, N$_2$, O$_2$, CO, CO$_2$, H$_2$O and inert gases, especially off-gases from adipic acid plants, and it can be selectively decomposed to the elements nitrogen and oxygen with negligible decomposition of other nitrogen oxides to the elements. The content of nitrogen oxides NO$_x$ can, as a rule, be 0–50%, preferably 1–40%, particularly preferably 10–30%, by volume and the N$_2$O content can, as a rule, be 0.01–65%, preferably 1–55%, particularly preferably 5–45%, by volume. It is possible, for example, to decompose dinitrogen monoxide mixed with, for example, 20% water and 65% nitrogen dioxide (NO$_2$) selectively into the elements.

Suitable catalysts are those which can be prepared by combining CuAl$_2$O$_4$ with the element as such or oxides or salts of tin, lead, an element of group IIa or IIb of the Periodic Table of the Elements, and, calcining at 300°–1300° C. under 0.1–200 bar. These catalysts contain no noble metals (Ag, Au, Pd, Pt) and have a BET surface area of 1–350 m$^2$/g.

The starting material may be a solid oxide which is wholly or partly, ie. 1–100%, preferably 10–90%, particularly preferably 20–70%, by weight, a spinel of the composition CuAl$_2$O$_4$ in an Al$_2$O$_3$ matrix, and this can be mixed with the same or higher concentration of tin, lead, an element of group IIa or IIb of the Periodic Table of the Elements, as oxide or salt or in elemental form, and calcined at 300°–1300° C., preferably 500°–1200° C., particularly preferably 600°–1100° C., under 0.1–200 bar, preferably 0.5–10 bar, particularly preferably under atmospheric pressure.

The mixing can take place, for example, by spraying, mechanical mixing, stirring or kneading the ground solid of the composition CuAl$_2$O$_4$, preferably in AL$_2$O$_3$, particularly preferably in Al$_2$O$_3$, or preferably by impregnating an unground solid of the composition CuAl$_2$O$_4$, preferably in Al$_2$O$_3$, particularly preferably in $\gamma$-Al$_2$O$_3$, with tin, lead, an element of group IIa or IIb of the Periodic Table of the Elements as oxide or salt (eg. in solution) or in elemental form.

The liberation of the copper in the form of the element or oxide, which usually leads to fine-particle dispersion, can be induced by partial (>50 mol %, preferably 70 mol %, particularly preferably >90 mol %) or complete (100 mol %) replacement of the copper in the spinel in the calcination step by tin, lead, an element of group IIa or IIb of the Periodic Table of the Elements in the form of the element, an oxide or salt-like compound if the resulting spinel is more thermodynamically stable than the original spinel CuAl$_2$O$_4$. The copper or copper oxide content in the catalyst ready for use is 0.1–50%, preferably 1–40%, particularly preferably 5–30%, by weight.

The elements of group IIa or IIb of the Periodic Table of the Elements can be used in the form of oxides or salt-like compounds or of the element as such (in metallic form). Examples of salt-like compounds are carbonates, hydroxides, carboxylates, halides and oxo anions such as nitrites, nitrates, sulfites, sulfates, phosphites, phosphates, pyrophosphates, halites, halates and basic carbonates, preferably carbonates, hydroxides, carboxylates, nitrites, nitrates, sulfates, phosphates and basic carbonates, particularly preferably carbonates, hydroxides, basic carbonates and nitrates, preferably in the +2 oxidation state such as Zn$^{2+}$, Mg$^{2+}$, Ca$^{2+}$, Sr$^{2+}$ and Ba$^{2+}$, especially Zn$^{2+}$ and Mg$^{2+}$ or mixtures thereof.

The preparation of the starting oxide of the composition CuAl$_2$O$_4$, preferably in the form of a spinel, is disclosed, for example, in Z. Phys. Chem., 141 (1984), 101–103. It proves advantageous to impregnate an Al$_2$O$_3$ carrier with a soluble compound such as a salt of the cation R, eg. a nitrite, nitrate, sulfite, sulfate, carbonate, hydroxide, carboxylate, halide, halite or halate, and subsequently to decompose the anion to the oxide thermally. Another possibility comprises mixing a compound such as a salt of the cation R with an oxygen-containing aluminum compound, eg. by drying or in suspension, especially by spray-drying, compacting the material, eg. by kneading, where appropriate by adding a suitable molding aid, molding by extrusion, drying and subsequently calcining to form the spinel. The calcination can be carried out at 300°–1300° C., preferably 600°–1000° C.

Doping of aluminum oxide carriers with a large surface area, is. the formation of mixed oxides, increases the thermal stability of the carrier (eg. DE-A-34 03 328, DE-A-25 00 548, Appl. Catal. 7 (1983) 211–220, J. Catal. 127 (1991) 595–604). The foreign ions may additionally contribute to the catalytic activity of the catalyst. The following elements may generally be employed for the doping: alkali metals, alkaline earth metals, rare earth metals, Sc, Ti, V, Cr, Mn, Fe, Co, Ni, Zn, Y, Zr, B, Si, Ge, Sn, Pb, P, Bi. The degree of replacement of aluminum oxide can be, for example, 0.01–20% by weight.

The size of the copper oxide crystallites in the unused catalyst is 1–100 nm, preferably 3–70 nm, particularly preferably 5–50 nm. The size can be determined, for example, by XRD (X-ray diffraction) or TEM (transmission electron microscopy).

The catalysts according to the invention contain mesopores of 2–20 nm and macropores of more than 20 nm and have BET surface areas of 1–350 m$^2$/g, preferably 10–200 m$^2$/g, particularly preferably 25–150 m$^2$/g, and porosity of 0.01–0.8 ml/g.

The catalysts which are preferably employed in the process according to the invention generally contain 0.1–50%, in particular 2–30%, by weight of copper oxide based on the weight of the aluminum oxide. The spinel-forming metal is present in a concentration which is the same as or higher than that of copper (mol/mol).

The GHSV is, as a rule, 500–50,000 l (STP) gas/l cat*h, preferably 1500–20,000 l (STP) gas/l cat*h.

EXAMPLES

Decomposition of dinitrogen monoxide a) The apparatus used for the adiabatic procedure is a Hasteloy C reaction tube which is 800 mm long and is divided into heating and reaction zones. The internal diameter is 18 mm. In order to be able to measure the temperature profile in the tube, an inner tube which has an external diameter of 3.17 mm and in which a thermoelement can easily be displaced was inserted. To improve heat transfer, the reactor was packed with inert material (steatite) in the heating zone.

b) Alternatively, however, the reaction can also be carried out under quasi-isothermal conditions in a salt bath reactor. The heat transfer agent is a melt composed of 53% by weight KNO$_3$, 40% by weight NaNO$_2$ and 7% by weight NaNO$_3$. The decomposition is carried out in a Hasteloy C reaction tube which is 600 mm long. The internal diameter is 14 mm. The gas is heated to the reaction temperature in a longer preheating zone. In order to be able to measure the temperature profile in the tube, once again an inner tube which has an external diameter of 3.17 mm and in which a thermoelement can easily be displaced was inserted.

In each case 40 ml of catalyst (1.5–2 mm chips) were tested.

The decomposition of N$_2$O in a gas mixture typical of the off-gas from an adipic acid plant was tested.

Typical gas composition:

N$_2$O: 23% by volume
NO$_2$: 17% by volume
N$_2$: 47% by volume
O$_2$: 7.5% by volume
H$_2$O: 3% by volume
CO$_2$: 2.5% by volume
GHSV: 4,000 l (STP) gas/l cat*h Preparation of the catalysts

EXAMPLE 1

A mixture of 284 g of Puralox® SCF (from Condea), 166 g of Pural® SB (from Condea) and 100 g of CuO (from Merck) was headed with 20 ml of formic acid (dissolved in 140 ml of H$_2$O) for 0.75 h, extruded to 3 mm extrudates, dried and calcined at 800° C. for 4 h.

71.4 g of the CuAl$_2$O$_4$-containing aluminum oxide carrier (water uptake: 69.1%) were impregnated twice with 49 ml of an aqueous solution which contained nitric acid (pH 3) and 32.6 g of Zn(NO$_3$)$_2$ and then left at room temperature for one hour. The impregnated carrier was dried to constant weight at 120° C. and finally calcined at 600° C. for 4 h.

EXAMPLE 2

A mixture of 346 g of Puralox® SCF (from Condea), 180 g of Pural® SB (from Condea) and 120 g of CuO (from Merck) was headed with 18 ml of formic acid (dissolved in 390 ml of H$_2$O) for I h, extruded to 3 mm extrudates, dried and calcined at 800° C. for 4 h.

85.2 g of the CuAl$_2$O$_4$-containing aluminum oxide carrier (water uptake: 70%) were impregnated three times with 47 ml of an aqueous solution which contained nitric acid (pH 2.5) and 45.2 g of Mg(NO$_3$)$_2$.6 H$_2$O and then left at room temperature for one hour. The impregnated carrier was dried to constant weight at 120° C. and finally calcined at 700° C. for 4 h.

EXAMPLE 3

A mixture of 288.4 g of Puralox® SCF (from Condea), 350 g of Pural® SB (from Condea) and 140 g of CuO (from Merck) was headed with 25 ml of formic acid (dissolved in 530 ml of H$_2$O) for 1 h, extruded to 3 mm extrudates, dried and calcined at 800° C. for 4 h.

65.9 g of the CuAl$_2$O$_4$-containing aluminum oxide carrier (water uptake: 60.3%) were impregnated twice with 47 ml of an aqueous solution which contained nitric acid (pH 3.1) and 34.7 g of Ca(NO$_3$)$_2$ and then left at room temperature for one hour. The impregnated carrier was dried to constant weight at 120° C. and finally calcined at 700° C for 4 h.

COMPARATIVE EXAMPLE 1

A catalyst was prepared as described in DE-A-40 29 061. 150 g of commercial aluminum oxide carrier (BET surface area 1.7 m$^2$/g; water uptake 29.2% by weight) was impregnated with 100 ml of aqueous solution which contained 41.7 g of AgNO$_3$ and then left to stand at room temperature for one hour. The impregnated carrier was dried to constant weight at 120° C. and finally calcined at 700° C. for 4 h. The catalyst obtained in this way contained 14.6% by weight of silver and had a BET surface area of 1.12 m$^2$/g.

COMPARATIVE EXAMPLE 2

The palladium catalyst on alpha-aluminum oxide preferred in DE-A-35 43 640 was prepared. 200 g of galpha-aluminum oxide (BET surface area 20.2 m$^2$/g) were impregnated with NaOH and dried at 120° C. This carrier was impregnated with 96 ml of an aqueous sodium tetrachloropalladate(II) solution containing 1.29 g of Pd and then left to stand at room temperature for three hours. The Pd$^{2+}$-containing carrier was treated with hydrazine to reduce the Pd$^{2+}$. The catalyst was subsequently washed until free of chlorine and dried to constant weight at 120° C. The catalyst obtained in this way contained 0.64% by weight of palladium.

COMPARATIVE EXAMPLE 3

A catalyst was prepared as described in DE-A-41 28 629. 225 g of Pural® SB were kneaded with 25 g of La(NO$_3$)$_3$ and 12.5 g of formic acid for 3 h, extruded, dried and calcined. 64.10 g of this (BET surface area 183 m$^2$/g; water uptake 76% by weight) were impregnated with 50.9 ml of an aqueous solution which contained 17.8 g of AgNO$_3$ and then left to stand at room temperature for one hour. The impregnated carrier was dried to constant weight at 120° C. and finally calcined at 700° C. for 4 h. The catalyst obtained in this way contained 14.5% by weight of silver and had a BET surface area of 156 m$^2$/g.

Test results a) Adiabatic process

| Catalyst | Running time (h) | Temperature (°C.) | Conversion (%) |
| --- | --- | --- | --- |
| 1 | 1036 | 480 | >99.9 |
| 2 | 1025 | 485 | >99.9 |
| 3 | 1013 | 485 | >99.9 |
| C1 | 150 | 610 | 97.5 |
| C2 | 112 | 640 | 66.5 |
| C3 | 280 | 530 | >99.9 |

The test results (catalysts 1 to 3) make it clear that the newly developed silver-free catalysts are both more active and more stable in an adiabatic process than are prior art catalysts C1 to C3.

| Catalyst | Running time (h) | Salt bath temperature (°C.) | N$_2$O conversion (%) |
| --- | --- | --- | --- |
| 1 | 48 | 540 | 98.0 |
| 2 | 48 | 540 | 97.2 |
| 3 | 48 | 540 | 97.4 |
| C3 | 48 | 540 | 41.0 |

The test results (catalysts 1 to 3) show that differences in activity are much more clearly evident in an isothermal process than in an adiabatic process where the energy released by the decomposition of N$_2$O makes a large contribution to the decomposition. The superiority of the newly developed silver-free catalysts compared with prior art catalysts C1 to C3 can be clearly demonstrated by carrying out an isothermal reaction.

We claim:

1. A process for the catalytic decomposition of dinitrogen monoxide in a gas stream which comprises contacting the gas stream at temperatures of 200°–900° C. and pressures of 0.1 to 20 bar with a catalyst free of noble metals, said catalyst being prepared by combining a spinel CuAl$_2$O$_4$ in an Al$_2$O$_3$ matrix with an additional spinel-forming metal component selected from the group consisting of tin, lead, zinc, magnesium, calcium, strontium and barium or mixtures thereof in elemental form or as an oxide or salt, and calcining at temperatures of 300°–1300° C. and under pressures of 0 1–200 bar for partial or complete liberation of the copper from said spinel in the form of its oxide by replacement with said additional metal component.

2. A process as claimed in claim 1, wherein said metal component is present as the oxide in the 2+ oxidation state when replacing the copper oxide of the spinel.

3. A process as claimed in claim 1, wherein said metal component is selected from the group consisting of zinc, magnesium, calcium, strontium and barium or mixtures thereof.

4. A process as claimed in claim 3, wherein said metal component is zinc magnesium or mixtures thereof.

5. A process as claimed in claim 3, wherein the metal component is zinc.

6. A process as claimed in claim 1, wherein the catalyst has a BET surface area of 1–350 m$^2$/g.

7. A process as claimed in claim 1, wherein the catalyst has a CuO content of 0.1–50% by weight.

8. A process as claimed in claim 1, wherein the porosity of the catalyst is 0.01–0.8 ml/g.

9. A process as claimed in claim 1, wherein the gas stream contacted with said catalyst contains up to 50% by volume of other nitrogen oxides.

10. A process as claimed in claim 1, wherein the gas stream contacted with said catalyst contains from 0.01–65% by volume of dinitrogen monoxide.

11. A process as claimed in claim 1, wherein the catalyst contains 1–40% by weight of copper oxide, based on the weight of the aluminum oxide, and the additional metal is present in a molar concentration which is the same or higher than that of copper.

12. A process as claimed in claim 11, wherein the catalyst contains mesopores of 2–20 nm and macropores of more than 20 nm and has a BET surface area of from 10–200 m$^2$/g and a porosity of 0.01-0.8 ml/g.

* * * * *